United States Patent
Sumida (10) Patent No.: US 10,814,116 B2
(45) Date of Patent: Oct. 27, 2020

(54) HOLLOW NEEDLE DEVICE (71) Applicant: TOPPAN PRINTING CO., LTD., Taito-ku (JP)

(72) Inventor: Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 557 days.

(21) Appl. No.: 14/990,865

(22) Filed: Jan. 8, 2016

(65) Prior Publication Data

US 2016/0114144 A1 Apr. 28, 2016

Related U.S. Application Data

(63) Continuation of application No. PCT/JP2014/068232, filed on Jul. 8, 2014.

(30) Foreign Application Priority Data

Jul. 8, 2013 (JP) .................................. 2013-142526

(51) Int. Cl.
*A61M 37/00* (2006.01)
*A61M 5/32* (2006.01)
*A61M 5/34* (2006.01)

(52) U.S. Cl.
CPC ...... *A61M 37/0015* (2013.01); *A61M 5/3293* (2013.01); *A61M 5/3298* (2013.01);
(Continued)

(58) Field of Classification Search
CPC .. A61M 5/3293; A61M 5/3286; A61M 5/345; A61M 5/3298; A61M 37/0015;
(Continued)

(56) References Cited

U.S. PATENT DOCUMENTS

2003/0050602 A1 3/2003 Pettis et al.
2009/0157041 A1 6/2009 Pettis et al.
(Continued)

FOREIGN PATENT DOCUMENTS

JP 2005-021677 A 1/2005
JP 2005-527249 A 9/2005
(Continued)

OTHER PUBLICATIONS

Extended European Search Report dated Feb. 6, 2017 in Patent Application No. 14822613.7.
(Continued)

*Primary Examiner* — Manuel A Mendez
*Assistant Examiner* — Justin L Zamory
(74) *Attorney, Agent, or Firm* — Oblon, McClelland, Maier & Neustadt, L.L.P.

(57) ABSTRACT

A hollow needle device includes a main body having a first surface on which hollow acicular bodies are formed and a second surface opposite to the first surface, a main body supporting member having an opening that accommodates the main body and including a drop-out prevention mechanism for holding the main body that has the hollow acicular bodies being protruded from one end of the opening, an injector supporting member disposed detachably in the opening of the main body supporting member, and a liquid-tight structure that establishes liquid tightness between the injector supporting member and an inner surface that defines the opening in the main body supporting member. The injector supporting member has a connection hole to which a protrusion of an injector is detachably connected liquid tightly to guide an injection solution supplied from the injector into the opening via the protrusion of the injector.

20 Claims, 3 Drawing Sheets

(52) U.S. Cl.
CPC ........... *A61M 5/3286* (2013.01); *A61M 5/345* (2013.01); *A61M 2037/0023* (2013.01)

(58) Field of Classification Search
CPC .. A61M 2037/0023; A61M 2037/0061; A61M 2037/003; A61M 2037/0046
See application file for complete search history.

(56) References Cited

U.S. PATENT DOCUMENTS

| | | |
|---|---|---|
| 2010/0030152 A1 | 2/2010 | Lee et al. |
| 2010/0286618 A1 | 11/2010 | Choi |
| 2011/0202035 A1* | 8/2011 | Voellmicke ........... A61M 5/008 604/506 |
| 2012/0123387 A1 | 5/2012 | Gonzalez et al. |
| 2012/0296280 A1 | 11/2012 | Eum |
| 2014/0052067 A1 | 2/2014 | Sausse et al. |

FOREIGN PATENT DOCUMENTS

| | | |
|---|---|---|
| JP | 2010-508058 A | 3/2010 |
| JP | 2011-509735 A | 3/2011 |
| JP | 2013-500773 A | 1/2013 |
| JP | 2013-90808 A | 5/2013 |
| WO | WO 2012/126784 A1 | 9/2012 |

OTHER PUBLICATIONS

International Search Report dated Sep. 16, 2014 in PCT/JP2014/068232, filed Jul. 8, 2014.

* cited by examiner

HOLLOW NEEDLE DEVICE

CROSS-REFERENCE TO RELATED APPLICATIONS

The present application is a continuation of International Application No. PCT/JP2014/068232, filed Jul. 8, 2014, which is based upon and claims the benefits of priority to Japanese Application No. 2013-142526, filed Jul. 8, 2013. The entire contents of these applications are incorporated herein by reference.

BACKGROUND OF THE INVENTION

Field of the Invention

The present invention relates to a hollow needle device.

Discussion of the Background

As equipment used for injecting an in-body injection solution, such as a liquid medicine or a vaccine, into a body of an animal including human, an injector provided with an injection needle has been widely known. The injector includes a combination of an outer cylinder having an inner hole for accommodating the in-body injection solution and a plunger disposed slidably in the inner hole of the outer cylinder. The plunger protrudes externally from one end of the inner hole. At the other end of the outer cylinder, a protrusion for attaching the injection needle is provided. A through hole is provided at the protrusion for attaching the injection, communicating with the other end of the inner hole of the outer cylinder. The base end section of the injection needle is attached to the protrusion for attaching the injection of the outer cylinder of the injector. The tip portion of the injection needle is pierced into the subcutaneous tissue of an animal, including human, and then the plunger of the injector is pressed, thereby injecting the in-body injection solution, stored in the inner hole of the outer cylinder of the injector, into the animal body.

An experienced technique is required for piercing with the tip portion of the injection needle, without causing large pain and bleeding, into the subcutaneous tissue of the animal. In a case where the injection needle is reused, it has been apparent that the re-used injection needle has a high probability of causing various infectious diseases in the animals where the re-used injection needle is inserted. Further, when the injection needle is disposed of, it has been apparent that the disposed injection needle has a high probability of hurting persons involved in a disposal process and cause various infectious diseases to the person who is hurt.

Recently, a multi-needle device has been used instead of a conventional injection needle. The multi-needle device is formed such that a plurality of acicular bodies of a micron scale are formed on a plate-like supporting body.

By setting the length of the plurality of acicular bodies to be within a range of the thickness of intradermal tissue, the plurality of acicular bodies can pierce into the intradermal tissue (i.e., epidermis and dermis), without causing large pain and bleeding when the plurality of acicular bodies are pressed onto the surface of the animal skin.

In a case where such a multi-needle device is used to inject the in-body injection solution into the intradermal tissue of the animal, the in-body injection solution is coated in advance on a portion of the animal skin where the in-body injection solution is injected, and then a plurality of acicular bodies of the multi-needle device is pierced into the above-described portion, or the in-body injection solution is coated to the plurality of acicular bodies in advance before the plurality of acicular bodies is pierced into the above-described portion.

In the intradermal tissue, since an abundance of antigen-presenting cells exists, an amount of the in-body injection solution to be used could be reduced compared to the conventional amount of use, when the in-body injection solution effecting on the antigen-presenting cells is injected into the intradermal tissue of the animal.

Japanese Patent Application Laid-Open Publication No. 2005-21677 (Patent Literature 1) discloses a pad base for transdermal drug administration in which a plurality of fine needles (acicular bodies) are provided on a skin-side surface of the skin patch base material. Each of the plurality of fine needles is made of biodegradable resin. Respective tip portions of the plurality of fine needles are horizontally cut. In the respective fine needles, a bottomed hole is formed in order to hold drugs from the horizontal cut surface to a vicinity of the base end portion of the respective fine needles. Alternatively, the respective fine needles are formed of biodegradable resin where a transdermally administrable drug is mixed thereto.

The pad base for transdermal drug administration can be produced at low cost in large quantities with a transfer molding such as mold injection, an imprint, casting or the like. Such a pad base for transdermal drug administration can be thrown away once it is used so that an occurrence of infectious diseases due to re-use can be prevented. Also, the fine needles have short lengths and respective tip portions are horizontally cut. Moreover, the plurality of fine needles are formed on the pad base with relatively high density. This type of pad base for transdermal drug administration significantly reduces chances of hurting the person involved in a process of disposal when disposing of it, and also the person involved in the disposal process can be significantly prevented from being infected from various infectious diseases.

However, since the conventional pad base is constituted such that a desired transdermal administration drug is injected into the intradermal tissue of the animal over a relatively long period of time, it is not suitable for injecting a precise desired amount of an desired drug into the intradermal tissue of the animal in a short period of time.

Japanese Patent Application Laid-Open Publication No. 2013-500773 (Patent Literature 2) discloses a hollow microneedle array having a structure suitable for injecting a desired amount of in-body injection solution into the intradermal tissue of an animal in a short period of time.

According to the hollow micro needle array, a plate spring in which one end is fixed to the back surface of the board is extended along the back surface of the board and a multi-needle device is attached to the other end of the plate spring. Normally, the plate spring is held in a state where the other end is elastically bent at a position away from the back surface of the substrate. A medicament cartridge storing a drug as a predetermined amount of in-body injection solution is disposed at one end of the plate spring. The medicament cartridge is urged by spring towards an acicular inlet protrusion of the multi-needle device at the other end of the plate spring. However, while the plate spring is being bent as described above, the medicament cartridge is held at a position away from the acicular inlet protrusion of the multi-needle device at the other end of the plate spring, resisting against the urging force of the spring.

When the above-described hold on the other end of the plate spring is released after the front surface of the board is brought into contact with a region to be injected with an in-body injection solution on the surface of the animal skin, the multi-needle device at the other end of the plate spring hit onto the above-described region of the animal skin by the elastic force accumulated in the plate spring, thereby piercing the multi-needles into the above-described region. At the same time, the above-described hold on the medicament cartridge is released to rapidly move the medicament cartridge, by the urging force of the above-described spring, towards the acicular inlet protrusion of the multi-needle device at the other end of the plate spring from the one end of the plate spring. Then, the medicament cartridge hits onto the acicular inlet protrusion. As a result, the drug stored in the medicament cartridge is supplied to the multi-needle device, and the drug in the medicament cartridge is injected into the intradermal tissue of the above-described region of the animal skin via the multiple needles of the multi-needle device.

The hollow microneedle array disclosed in Japanese Patent Application Laid-Open Publication No. 2013-500773 (Patent Literature 2) has a complex configuration and only a dedicated medicament cartridge can be used. Further, the amount of drug stored in advance in the medicament cartridge is difficult to change.

Patent Literature 1: Japanese Patent Application Laid-Open Publication No. 2005-21677
Patent Literature 2: Japanese Patent Application Laid-Open Publication No. 2013-500773

SUMMARY OF THE INVENTION

According to one aspect of the present invention, a hollow needle device includes a main body having a first surface on which hollow acicular bodies are formed and a second surface opposite to the first surface, a main body supporting member having an opening that accommodates the main body and including a drop-out prevention mechanism for holding the main body that has the hollow acicular bodies being protruded from one end of the opening, an injector supporting member disposed detachably in the opening of the main body supporting member such that the injector supporting member faces the second surface of the main body on an opposite side of the one end, and a liquid-tight structure that establishes liquid tightness between the injector supporting member and an inner surface that defines the opening in the main body supporting member. The injector supporting member has a connection hole to which a protrusion of an injector is detachably connected liquid tightly to guide an injection solution supplied from the injector into the opening via the protrusion of the injector.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

Figure 1:
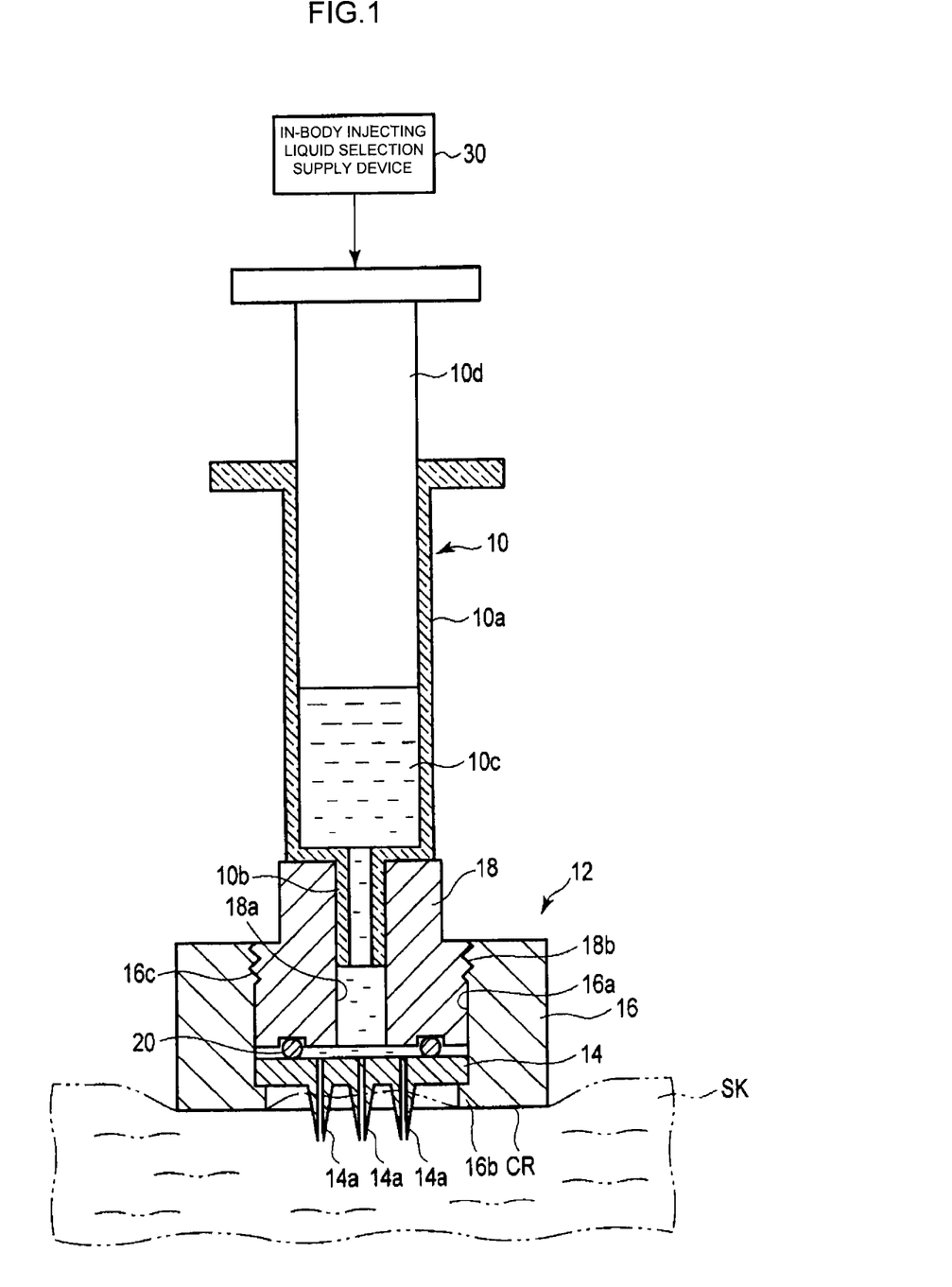
FIG. 1 is a vertical cross sectional view schematically showing a hollow needle device according to an embodiment of the invention which is combined with a conventional injector, in a state immediately before an intradermal injection is performed.

First, with reference to FIG. 1, a configuration of a hollow needle device 12 according to an embodiment of the present invention which is combined with a conventional injector 10 is described.

The conventional injector 10 includes a combination of an outer cylinder 10a having an inner hole for accommodating an in-body injection solution 10c, and a plunger 10d disposed slidably in an inner hole of the outer cylinder 10a and externally extended from one end of the inner hole. At the other end of the outer cylinder 10a, an injection needle attachment protrusion 10b is provided. At the injection needle attachment protrusion 10b, a through hole that communicates with the other end of the inner hole of the outer cylinder 10a is provided.

The hollow needle device 12 is provided with a main body 14 having one surface where a plurality of hollow acicular bodies 14a are formed and the other surface opposite to the one surface. In the present embodiment, the main body 14 has a disc shape having a predetermined diameter.

As for the main body 14, at least, a plurality of hollow acicular bodies 14a is made of a biocompatible material and preferably, an entire main body 14 including a plurality of acicular bodies is integrally formed of a biocompatible material. Known biocompatible materials include, for example, a metal material such as stainless steel, titanium, manganese or the like, resin materials such as a medical-use silicone, polyglycolic acid, polycarbonate or the like, and inorganic materials such as silicon.

To integrally form the entire main body 14 including a plurality of hollow acicular bodies 14a with a biocompatible material, for example, conventional molding techniques such as insert molding, extrusion molding, imprinting, hot embossing and casting can be used. For the respective plurality of hollow acicular bodies 14a, for example, by using conventional micro drilling process techniques such as microdrilling, laser processing or the like, through holes are formed between the other surface of the main body 14 and respective outer surfaces corresponding to the plurality of hollow acicular bodies 14a so as to extend along center axes of the respective hollow acicular bodies 14a. The through holes may be or may not be concentric circles with respect to the central axis of the respective hollow acicular bodies 14a.

The overall shape of the plurality of hollow acicular bodies 14a may be, for example, a cone shape, a pyramidal shape including a triangular pyramid and a quadrangular pyramid, or a column or a prism having a sharp tip portion.

The hollow needle device 12 further includes a main body supporting member 16. In the main body supporting member 16, a main body accommodating opening 16a is formed, in which the main body 14 is accommodated. In the main body accommodating opening 16a, a drop-out prevention mechanism 16b is provided. The drop-out prevention mechanism 16b prevents the main body 14 accommodated in the main body accommodating opening 16a from dropping out from the one end, with the plurality of hollow acicular bodies 14a being protruded from one end of the main body accommodating opening 16a.

Also, the main body supporting member 16 is made of a biocompatible material similar to that of the main body 14. As a biocompatible material for the main body supporting member 16, glass can be employed.

In more detail, according to the present embodiment, the main body supporting member 16 has a substantially cylindrical shape. The main body accommodating opening 16a has a circular cross section having a diameter slightly larger than that of the main body 14, in order to accommodate the main body 14 having a disc shape as described above. The main body accommodating opening 16a is extended along the center line of the main body supporting member 16 having the cylindrical shape and has openings at both end surfaces of the main body supporting member 16.

In an inner peripheral surface of the main body accommodating opening 16a, an inward flange is formed at a portion adjacent to the one end. This inward flange provides the drop-out prevention mechanism 16b.

While the main body 14 is accommodated in the main body accommodating opening 16a of the main body supporting member 16 and prevented, by the drop-out prevention mechanism 16b of the main body accommodating opening 16a, from dropping out from the one end, the plurality of hollow acicular bodies 14a of the main body 14 are protruded, as described above, externally from a region surrounded by the inward flange at the one end of the main body accommodating opening 16a. The respective heights of the protrusions of the plurality of hollow acicular bodies 14a from the one end of the main body accommodating opening 16a are set to be within a thickness of the intradermal tissue of an animal, including human.

The hollow needle device 12 further includes an injector supporting member 18. The injector supporting member 18 is disposed detachably in the main body accommodating opening 16a of the main body supporting member 16, facing the other surface of the main body 14 at an opposite side of the one end. Further, the injector supporting member 18 includes an injection needle attachment protrusion connection hole 18a to which the injection needle attachment protrusion 10b of the outer cylinder 10a of the conventional injector 10 is detachably connected liquid tightly. The injection needle attachment protrusion connection hole 18a guides the in-body injection solution 10c flowing from an inner hole of the outer cylinder 10a of the injector 10 via the through hole of the injection needle attachment protrusion 10b, into the main body accommodating opening 16a.

In the inner peripheral surface of the injection needle attachment protrusion connection hole 18a, a region to which the injection needle attachment protrusion 10b of the outer cylinder of the conventional injector 10 is detachably connected liquid tightly preferably has a taper shape conforming to the luer lock standard.

The injector supporting member 18 according to the present embodiment has a substantially cylindrical shape having an outer diameter which is substantially the same as the diameter of the inner peripheral surface of the main body accommodating opening 16a of the main body supporting member 16.

According to the present embodiment, a female screw 16c is formed at a portion adjacent to the other end of the inner peripheral surface of the main body accommodating opening 16a of the main body supporting member 16 and a male screw 18b threadably engaged with the female screw 16c is formed on the outer peripheral surface of the injector supporting member 18. In other words, according to the present embodiment, the male screw 18b of the outer peripheral surface of the injector supporting member 18 is threadably engaged with the female screw 16c formed at a portion adjacent to the other end of the inner peripheral surface of the main body accommodating opening 16a of the main body supporting member 16, whereby the injector supporting member 18 is disposed detachably in the main body accommodating opening 16a of the main body supporting member 16, facing the other surface of the main body 14 at an opposite side of the one end.

Other than the combination of the above-described female screw 16c and the male screw 18b, various detachable arrangement mechanisms in the known art can be used for the mechanism in which the injector supporting member 18 is disposed detachably in the main body accommodating opening 16a of the main body supporting member 16, facing the other surface of the main body 14 on an opposite side of the one end. For example, the detachable arrangement mechanisms include a snap coupling structure, an independent fixed screw, a combination of the fixed screw and a retaining plate or the like.

The hollow needle device 12 further includes a liquid-tight structure 20 that establishes a liquid-tight relationship between a portion between the injector supporting member 18 and an inner surface that defines the main body accommodating opening 16a in the main body supporting member 16.

According to the present embodiment, the liquid-tight structure 20 is constituted of an annular liquid-tight member sandwiched between the other surface of the main body 14 and a portion facing the other surface of the main body 14 in the injector supporting member 18. The main body 14 is accommodated in the main body accommodating opening 16a of the main body supporting member 16, being prevented from dropping out from the one end by the drop-out prevention mechanism 16b of the main body accommodating opening 16a.

The liquid-tight structure 20 surrounds all openings of the above-described plurality of through holes formed in the plurality of hollow acicular bodies 14a at the other surface of the main body 14. For the annular liquid-tight member, an elastic body having circular shape, for example, an O-ring can be employed.

The annular liquid-tight members may be provided between the outer peripheral surface of the injector supporting member 18 and the inner peripheral surface of the main body accommodating opening 16a of the main body supporting member 16.

In the present embodiment, a portion being contacted with the in-body injection solution 10c is required to be coated with a substance which will not deteriorate the in-body injection solution 10c or will not be deteriorated by the in-body injection solution 10c or to be formed of such a substance.

Hereinafter, with reference to FIGS. 1 and 2, an operating procedure of the hollow needle body device 12 according to an embodiment constituted as described above will be described.

In the inner hole of the outer cylinder of the conventional injector 10, a desired amount of in-body injection solution 10c (for example, a liquid medicine or vaccine to be injected into the skin (i.e., epidermis and dermis) of an animal, including human) is sucked via the through hole of the injection needle attachment protrusion 10b and held therein. The conventional injector 10 can be made available easily and cheaply. The outer cylinder 10a of the conventional injector 10 is substantially transparent allowing the amount of the in-body injection solution 10c held in the inner hole to be visually recognized from outside. Moreover, a scale clearly indicating the amount is provided on the outer peripheral surface of the outer cylinder 10a. Therefore, by using the conventional injector 10, the amount of the in-body injection solution 10c held in the inner hole of the outer cylinder 10a of the conventional injector 10 can be changed precisely and easily.

As shown in FIG. 1, the injection needle attached protrusion 10b of the outer cylinder 10a of the injector 10 is detachably and liquid tightly connected to the injection-needle-attached protrusion connection hole 18a of the injector supporting member 18 in the hollow acicular body device 12. Subsequently, the plunger 10d of the injector 10 is slightly pressed and a small amount of the in-body injection solution 10c in the outer cylinder 10a of the injector 10 fills, via the through hole of the injection needle attached protrusion 10b of the outer cylinder 10a, the injection-needle-attached protrusion connection hole 18a of the injector supporting member 18 in the hollow acicular body device 12, a liquid tight region formed by the liquid-tight structure 20 in the main body accommodating opening 16a of the main body supporting member 16 as described above, and the through holes formed in the plurality of hollow acicular bodies 14a of the main body 14.

Next, as shown in FIG. 1, a circular end region (i.e., skin contact region) CR is pressed onto a surface of a region where the in-body injection solution 10c is desired to be injected (i.e., in-skin injecting region) in the intradermal tissue (i.e., epidermis and dermis) SK of an animal, including human, and the plurality of hollow acicular bodies 14a of the main body 14 are inserted into the in-skin injecting region. The circular end region (i.e., skin contact region) CR is located at the one end side of the main body accommodating opening 16a where the plurality of hollow acicular bodies 14a of the main body 14 are protruded from the outer surface of the main body supporting member 16 of the hollow needle device 12. While the circular end region CR is pressed, in the in-skin injecting region of the intradermal tissue SK, a portion surrounded by the circular end region (i.e., skin contact region) CR at the outer surface of the main body supporting member 16 in the hollow needle device 12 (i.e., a portion corresponding to the one end of the main body accommodating opening 16a) rises within the one end due to relaxation of the pressure applied from the circular end region (i.e., skin contact region) CR. As a result, the plurality of hollow acicular bodies 14a are pierced deeply into the surrounded portion of the in-skin injecting region in the intradermal tissue SK.

Figure 2:
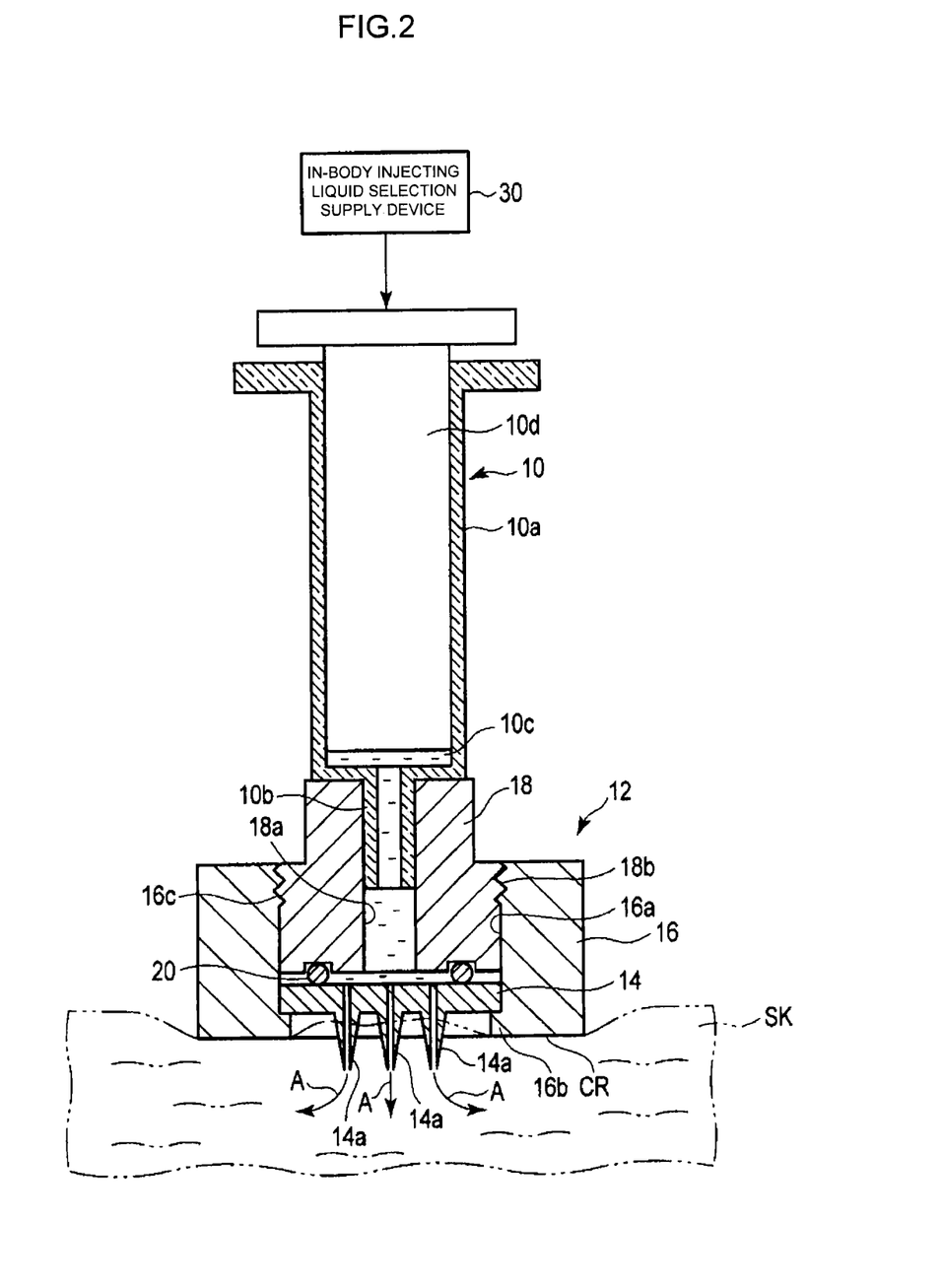
FIG. 2 is a vertical cross sectional view schematically showing the injector and the hollow needle device as shown in FIG. 1, in a state immediately after an intradermal injection is performed.

Next, as shown in FIG. 2, when further pressing the plunger 10d of the injector 10 for a predetermined distance, the rest of the desired amount of the in-body injection solution 10c in the outer cylinder 10a of the injector 10 is injected into the surrounded portion of the in-skin injecting region in the intradermal tissue SK as indicated by the arrow A, via the through hole of the injection needle attachment protrusion 10b of the outer cylinder 10a, the injection needle attachment protrusion connection hole 18a of the injector supporting member 18 in the hollow needle device 12, liquid tight region formed by the liquid-tight structure 20 in the plurality of hollow acicular bodies 14a of the main body supporting member 16 as described above, and the through holes of the plurality of hollow acicular bodies 14a of the main body 14. In the above-described portion, as mentioned above, the pressing force of the circular end region (i.e., skin contact region) CR of the outer surface of the main supporting member 16 in the hollow needle device 12 is relaxed. Accordingly, the in-body injection solution 10c supplied through the through holes of the plurality of hollow acicular bodies 14a is readily injected into the in-skin injecting region from the surface of the in-skin injecting region of the intradermal tissue SK without leaking outside.

It should be noted that the outer cylinder 10a of the conventional injector 10 is substantially transparent such that the amount of the in-body injection solution 10c held in the inner hole can be visually recognized from outside, and a scale is provided on the outer surface of the outer cylinder 10a to clearly indicate the amount. Accordingly, by using the hollow needle device 12 of the embodiment in combination with the conventional injector 10, a precise desired amount of desired in-body injection solution 10c can be injected into the intradermal tissue SK of the animal.

Figure 3:
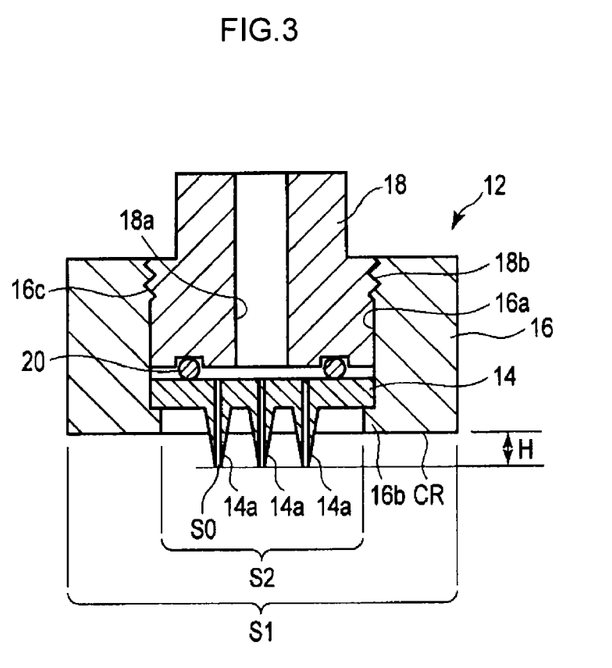
FIG. 3 is a vertical cross sectional view schematically showing an enlarged hollow needle device together with reference signs representing various dimensions and regions.

Next, with reference to FIG. 3, preferable various specific dimension examples of the hollow needle device 12 according to an embodiment constituted as described above will be described.

In the present embodiment, the height H of protrusion of each of the plurality of hollow acicular bodies 14a extending from the one end of the main body accommodating opening 16a of the main body supporting member 16 is preferably in a range from 0.3 mm to 2.0 mm and more preferably in a range from 0.5 mm to 1.5 mm. The height H of protrusion of each of the plurality of hollow acicular bodies 14a is set in this way, whereby pain sensed by an animal, including human, can be mitigated, when the plurality of hollow acicular bodies 14a are pierced into the surface of a region (i.e., in-skin injecting region) to which the in-body injection solution 10c is injected in the intradermal tissue (i.e., epidermis and dermis) SK of the animal. Moreover, it is understood that a desired amount of desired in-body injection solution 10c can be reliably injected into the in-skin injecting region from the respective through holes of the plurality of hollow acicular bodies 14a.

In the present embodiment, the opening area SO of each of the through holes at the respective protrusion ends of the plurality of hollow acicular bodies 14a is preferably within a range from 1000 $\mu m^2$ to 10000 $\mu m^2$. It is understood that the opening area SO having such a range is able to ensure a formation of the through holes with a conventional method as described above, and a desired amount of desired in-body injection solution 10c can be reliably injected into a region (i.e., in-skin injecting region) to which the in-body injection solution 10c is injected in the intradermal tissue (i.e., epidermis and dermis) SK of an animal, including human, from the respective through holes of the plurality of hollow acicular bodies 14a.

In the outer surface of the main body supporting member 16 of the present embodiment, a sum total S1 of the area of the circular end region (i.e., skin contact region) CR at a side where the one end is opened in the main body accommodating opening 16a and an area S2 of the one end is preferably in a range from 0.10 $cm^2$ to 5.0 $cm^2$. In the one surface of the main body 14, the area S2 of an exposed region exposed to the one end of the main body accommodating opening 16a of the main body supporting member 16 is preferably in a range from 0.05 $cm^2$ to 4.0 $cm^2$. Both of the area of the one end of the main body accommodating opening 16a and the area of the exposed region exposed to the one end of the main body accommodating opening 16a of the main body supporting member 16 in the one surface of the main body 14 are defined as the area S2.

By using a widely known processing method, it is difficult to produce the sum total S1 to be smaller than 0.10 $cm^2$ cheaply and reliably. The sum total S1 is composed of the area of the circular end region (i.e., skin contact region) CR of the outer surface in the main body supporting member 16 and the area S2 of the one end.

Similarly, by using a widely known processing method, it is difficult to produce the area S2 of an exposed region to be smaller than 0.05 cm$^2$ cheaply and reliably. The area S2 of an exposed region corresponds to the area S2 of the one end of the main body accommodating opening 16a and is exposed to the one end of the main body accommodating opening 16a of the main body supporting member 16 in the one surface of the main body 14.

In a case where the sum total S1 composed of the area of the circular end region (i.e., skin contact region) CR in the outer surface of the main body supporting member 16 and the area S2 of the one end of the main body accommodating opening 16a is larger than or equal to 5.0 cm$^2$, a long distance is created between the outermost periphery of the circular end region CR (i.e., skin contact region) of the outer surface in the main body supporting member 16 and each of the plurality of hollow acicular bodies 14a disposed at the outermost side in the exposed region exposing the one surface. As a result, the outermost located ones of the plurality of hollow acicular bodies 14a are no longer guaranteed to sufficiently pierce into the in-skin injecting region in the intradermal tissue (i.e., epidermis and dermis) SK of an animal.

Similarly, in a case where an exposed region is larger than or equal to 4.0 cm$^2$, a long distance is created between the outermost periphery of the circular end region CR (i.e., skin contact region) of the outer surface in the main body supporting member 16 and each of the plurality of hollow acicular bodies 14a disposed at the outermost side in the exposed region exposing the one surface. As a result, the outermost located ones of the plurality of hollow acicular bodies 14a are no longer guaranteed to sufficiently pierce into the in-skin injecting region in the intradermal tissue (i.e., epidermis and dermis) SK of an animal. The exposed region is where the one surface of the main body 14 is exposed from the one end of the main body accommodating opening 16a, corresponding to the area S2 of the one end of the main body accommodating opening 16a in the main body supporting member 16.

It is hard to use the hollow acicular body device 12 as a multi-needle device for injecting the in-body injection solution 10c into the intradermal tissue SK in a case where the sum total of the area of the circular end region (i.e., skin contact region) CR in the outer surface of the main body supporting member 16 and the area S2 of the one end of the main body accommodating opening 16a is larger than or equal to 5.0 cm$^2$, and in a case where an exposed region in the one surface of the main body 14 is larger than or equal to 4.0 cm$^2$, the exposed region being exposed from the one end of the main body accommodating opening 16a and corresponding to the area S2 of the one end of the main body accommodating opening 16a in the main body supporting member 16.

Modification

In the above-described embodiment, the skin contact region of the outer surface in the main body supporting member 16 of the hollow needle device 12 is pressed onto the surface of the in-skin injecting region of the intradermal tissue SK of an animal, including human, and then, the user presses the plunger 10d of the injector 10 while the plurality of hollow acicular bodies 14a of the main body 14 are pierced into the in-skin injecting region. Alternatively, during this period, as shown in FIG. 1, an in-body injection solution selection supply device 30 can press the plunger 10d.

This sort of in-body injection solution selection supply device 30 can be detachably fixed to the outer surface of the outer cylinder of the injector 10 or the outer surface of the injector supporting member 18, with a publicly known fixing means including a fixed screw or a clip which is not shown. The in-body injection solution selection supply device 30 is configured such that an externally exposed end of the plunger 10d provided at a protruding position as shown in FIG. 1 is selectively pressed. Such a configuration may include a drive member (not shown) that contacts or is in proximity the externally exposed end of the plunger 10d, an energizing force producing source (not shown) that produces an energizing force applied to the drive member towards the external exposed end of the plunger 10d and a switch mechanism (not shown) that makes the energizing force producing source (not shown) selectively produce the energizing force.

More specifically, the energizing force producing source (not shown) can be selected from, for example, a compression spring or a tension spring or an elastic material or a magnet or sources of a compressed gas including compressed air. Further, the switch mechanism that can be used includes a publicly known latching mechanism (mechanism that releases the energizing force by releasing the latch) in which a movement of the drive member (not shown) is suspended to resist against the energizing force from the energizing force producing source (not shown) or a trigger mechanism (mechanism that releases the energizing force by pulling the trigger) or a pressed metal mechanism (mechanism that releases the energizing force by pressing a pressed metal or a push button) or a hand-powered/electro-magnetic drive ON-OFF valve which is capable of selectively supplying a compressed gas from the compressed gas source including the compressed air to the drive member (not shown).

The present invention provides a hollow needle device having a simple configuration capable of being manufactured at low cost in which a precise desired amount of a desired in-body injection solution can be injected into the intradermal tissue of the animal in a short period of time, and capable of readily changing the desired amount of the desired in-body injection solution.

The purpose of the above-described invention is accomplished with a hollow needle device that injects an in-body injection solution into an intradermal tissue of an animal skin.

The hollow needle device is characterized by including: a main body having one surface where a plurality of hollow acicular bodies are formed and the other surface opposite to the one surface; a main body supporting member, wherein a main body accommodating opening that accommodates the main body is formed and a drop-out prevention mechanism is provided in the main body accommodating opening, the drop-out prevention mechanism preventing the main body accommodated in the main body accommodating opening from dropping out from the one end with the plurality of hollow acicular bodies being protruded from one end of the main body accommodating opening; an injector supporting member disposed detachably in the main body accommodating opening of the main body supporting member, facing the other surface of the main body at an opposite side of the one end, the injector supporting member including an injection needle attachment protrusion connection hole to which an injection needle attachment protrusion of an injector is detachably connected liquid tightly, and the injection needle attachment protrusion connection hole guiding the in-body injection solution supplied from the injector via the injection needle attachment protrusion, into the main body accommodating opening; and a liquid-tight structure that establishes liquid tightness between the injector supporting member and an inner surface that defines the main body accommodating space in the main body supporting member.

The above-described hollow needle device according to the present invention is used, with the injection needle attachment protrusion of the injector being detachably connected liquid tightly thereto. For the injector, a conventional injector may be used. Accordingly, a desired amount of a desired in-body injection solution can readily be changed precisely, and its configuration is simple and can be produced at low cost. Moreover, a desired amount of a desired in-body injection solution can be accurately injected into the intradermal tissue of an animal in a short period of time.

REFERENCE SIGNS LIST

10: injector
10a: outer cylinder
10b: injection needle attachment protrusion
10c: in-body injection solution 10c
10d: plunger
12: hollow needle device
14: main body
14a: hollow acicular bodies
16: main body supporting member
16a: main body accommodating opening
16b: drop-out prevention mechanism
16c: female screw
18: injector supporting member
18a: injection needle attachment protrusion connection hole
18b: male screw
20: liquid-tight structure
30: in-body injection solution selection supply device
SK: intradermal tissue
CR: end region (i.e., skin contact region)

Obviously, numerous modifications and variations of the present invention are possible in light of the above teachings. It is therefore to be understood that within the scope of the appended claims, the invention may be practiced otherwise than as specifically described herein.

What is claimed is:

1. A hollow needle device, comprising:
a main body having a plurality of hollow acicular bodies formed such that the hollow acicular bodies are protruding from a first surface of the main body;
a main body supporting member having an opening that accommodates the main body inside the main body supporting member, and an inward flange holding the first surface of the main body;
an injector supporting member disposed detachably in the opening of the main body supporting member such that the injector supporting member faces a second surface of the main body on an opposite side of the first surface; and
a liquid-tight structure positioned inside the opening between the injector supporting member and the second surface of the main body such that liquid tightness is established between the injector supporting member and an inner surface that defines the opening in the main body supporting member,
wherein the main body supporting member has an end surface having a skin contact region and the inward flange of the main body supporting member formed such that the first surface of the main body is recessed from the end surface having the skin contact region and that the hollow acicular bodies extend proximally from inside the opening and distally beyond the end surface having the skin contact region, and the injector supporting member has a connection hole to which a protrusion of an injector is detachably connected liquid tightly to guide an injection solution supplied from the injector into the opening via the protrusion of the injector.

2. The hollow needle device according to claim 1, further comprising:
a supply device configured to selectively press a plunger of the injector to supply the injection solution supplied from the injector via the protrusion into the opening and discharge the injection solution from the hollow acicular bodies, when the protrusion of the injector holding the injection solution is connected to the connection hole.

3. The hollow needle device according to claim 1, wherein the hollow acicular bodies comprise a biocompatible material.

4. The hollow needle device according to claim 2, wherein the hollow acicular bodies comprise a biocompatible material.

5. The hollow needle device according to claim 1, wherein the hollow acicular bodies are configured such that each of the hollow acicular bodies is protruded from the one end of the opening to have a height of protrusion in a range of from 0.3 mm to 2.0 mm.

6. The hollow needle device according to claim 5, wherein the height is in a range of from 0.5 mm to 1.5 mm.

7. The hollow needle device according to claim 2, wherein the hollow acicular bodies are configured such that each of the hollow acicular bodies is protruded from the one end of the opening to have a height of protrusion in a range of from 0.3 mm to 2.0 mm.

8. The hollow needle device according to claim 7, wherein the height is in a range of from 0.5 mm to 1.5 mm.

9. The hollow needle device according to claim 3, wherein the hollow acicular bodies are configured such that each of the hollow acicular bodies is protruded from the one end of the opening to have a height of protrusion in a range of from 0.3 mm to 2.0 mm.

10. The hollow needle device according to claim 9, wherein the height is in a range of from 0.5 mm to 1.5 mm.

11. The hollow needle device according to claim 1, wherein each of the hollow acicular bodies has a through hole having an opening area at a protrusion end in a range of from 1000 $\mu m^2$ to 10000 $\mu m^2$.

12. The hollow needle device according to claim 2, wherein each of the hollow acicular bodies has a through hole having an opening area at a protrusion end in a range of from 1000 $\mu m^2$ to 10000 $\mu m^2$.

13. The hollow needle device according to claim 3, wherein each of the hollow acicular bodies has a through hole having an opening area at a protrusion end in a range of from 1000 $\mu m^2$ to 10000 $\mu m^2$.

14. The hollow needle device according to claim 5, wherein each of the hollow acicular bodies has a through hole having an opening area at a protrusion end in a range of from 1000 $\mu m^2$ to 10000 $\mu m^2$.

15. The hollow needle device according to claim 1, wherein the main body supporting member has an outer surface having a circular end region on a side of the one end of the opening such that a sum of an area of the circular end region and an area of the opening on the one end is in a range of from 0.10 cm² to 5.0 cm², and that an area of an exposed region corresponding to the area of the opening on the one end is in a range from 0.05 cm² to 4.0 cm².

16. The hollow needle device according to claim 2, wherein the main body supporting member has an outer surface having a circular end region on a side of the one end of the opening such that a sum of an area of the circular end region and an area of the opening on the one end is in a range of from 0.10 cm² to 5.0 cm², and that an area of an exposed region corresponding to the area of the opening on the one end is in a range from 0.05 cm² to 4.0 cm².

17. The hollow needle device according to claim 3, wherein the main body supporting member has an outer surface having a circular end region on a side of the one end of the opening such that a sum of an area of the circular end region and an area of the opening on the one end is in a range of from 0.10 cm² to 5.0 cm², and that an area of an exposed region corresponding to the area of the opening on the one end is in a range from 0.05 cm² to 4.0 cm².

18. The hollow needle device according to claim 5, wherein the main body supporting member has an outer surface having a circular end region on a side of the one end of the opening such that a sum of an area of the circular end region and an area of the opening on the one end is in a range of from 0.10 cm² to 5.0 cm², and that an area of an exposed region corresponding to the area of the opening on the one end is in a range from 0.05 cm² to 4.0 cm².

19. The hollow needle device according to claim 1, wherein the liquid-tight structure comprises an elastic member.

20. The hollow needle device according to claim 1, wherein the liquid-tight structure comprises an annular member surrounding opening of the hollow acicular bodies on the second surface of the main body.

* * * * *